(12) United States Patent
Kryzpow et al.

(10) Patent No.: US 9,826,917 B1
(45) Date of Patent: *Nov. 28, 2017

(54) ELECTRODE HARNESS AND METHOD OF TAKING ELECTRICAL MEASUREMENTS

(75) Inventors: David Kryzpow, University Heights, OH (US); James Elliott, Streetsboro, OH (US); Aaron Rood, Rocky River, OH (US); Frederick J. Lisy, Euclid, OH (US)

(73) Assignee: Orbital Research Inc., Cleveland, OH (US)

( * ) Notice: Subject to any disclaimer, the term of this patent is extended or adjusted under 35 U.S.C. 154(b) by 1572 days.

This patent is subject to a terminal disclaimer.

(21) Appl. No.: 13/204,788

(22) Filed: Aug. 8, 2011

Related U.S. Application Data

(60) Continuation of application No. 11/305,948, filed on Dec. 19, 2005, now Pat. No. 8,019,402, which is a division of application No. 10/988,358, filed on Nov. 12, 2004, now Pat. No. 9,326,695.

(51) Int. Cl.
*A61B 5/0408* (2006.01)

(52) U.S. Cl.
CPC ........ *A61B 5/04085* (2013.01); *A61B 5/0408* (2013.01)

(58) Field of Classification Search
CPC .......................... A61B 5/0408; A61B 5/04085
See application file for complete search history.

(56) References Cited

U.S. PATENT DOCUMENTS

| | | | | |
|---|---|---|---|---|
| 6,611,705 B2* | 8/2003 | Hopman | ............... | A61B 5/0006 600/386 |
| 6,622,035 B1* | 9/2003 | Merilainen | ........ | A61B 5/04025 600/391 |
| 8,019,402 B1* | 9/2011 | Kryzpow | ........... | A61B 5/04085 600/386 |
| 9,326,695 B1* | 5/2016 | Kryzpow | ........... | A61B 5/04085 |

* cited by examiner

*Primary Examiner* — Lee S Cohen
(74) *Attorney, Agent, or Firm* — Brian Kolkowski

(57) ABSTRACT

The present invention relates to an electrode harness and more particularly to an electrode harness with various features, which enhance the use and performance of the electrode harness. The present invention further relates to a method of taking biopotential measurements. The electrode harness and methods of the present invention allow for use with most applications where biopotential measurements are taken. The electrode harness can be used in ECG (or EKG), EEG, EMG, and other such biopotential measurement applications. Because of the versatility of various embodiments of the present invention, preferably the electrode harness can be adjusted for different applications or for application to various sized and shaped subjects. The electrode harness is further preferably part of a system, which includes either wireless or tethered bridges between the electrode harness and a monitor, and preferably includes various forms of processors for analyzing the biopotential signal.

18 Claims, 14 Drawing Sheets

No. 11/305,948, which was filed on Dec. 19, 2005
ELECTRODE HARNESS AND METHOD OF TAKING ELECTRICAL MEASUREMENTS

CROSS-REFERENCE TO RELATED APPLICATIONS

This application is a continuation of U.S. patent application Ser. No. 11/305,948, which was filed on Dec. 19, 2005 and which issued as U.S. Pat. No. 8,019,402 on Sep. 13, 2011, which is a division of U.S. patent application Ser. No. 10/988,358, that was filed on Nov. 12, 2004 and which issued as U.S. Pat. No. 9,326,695 on May 3, 2016.

The U.S. Government has a paid-up license in this invention and the right in limited circumstances to require the patent owner to license others on reasonable terms provided for by the terms of contract number DMI-0216284 awarded by the National Science Foundation.

BACKGROUND OF THE INVENTION

1. Field of the Invention

The present invention relates to an electrode harness and more particularly to an electrode harness with various features, which enhance the use and performance of the electrode harness. The present invention further relates to a method of taking biopotential measurements.

2. Technical Background

Medical diagnostics include many tests that obtain biopotential measurements from the surface or just under the surface of the skin of a subject. These tests vary widely, ranging from the electro-cardiogram (EKG) that measures electric impulses generated by the heart, to the electroencephalogram (EEG) which measures electric impulses generated by the brain. These diagnostics, and a multitude of others, require electrodes to be placed on the skin of a subject. These electrodes, which routinely measure weak signals 100 microvolts or less for (EEG), must be very sensitive to accurately pick up such small signals. In addition, these electrodes are very sensitive to placement and contact with the subject's skin. Most biopotential monitoring systems today, generally speaking, require many different components, pieces, and operations to use. The more complicated these systems are the more time and manpower is required to operate and utilize them, and the greater the risk of inaccurate measurements.

More recently, electrode harnesses have been developed to integrate the placement of electrodes for various medical applications. The electrode harnesses, however, are simple and have not been very effective given most are difficult to use, and attempt to integrate existing electrode technology into their design. An example of this type of device is described in Jones et al. U.S. Pat. No. 4,595,013. Jones et al. describes an electrode harness wherein a plurality of electrodes are permanently mounted on a flexible adhesive-backed harness pad. Another example is described in U.S. Pat. No. 4,854,323 to Rubin wherein an electrode harness is described having a hollow tub for containing and housing the individual lead wires for each electrode and a flexible stylet which when bent, into a desired shape, will maintain that shape until reshaped. The individual electrodes are slideably adjustable about the exterior of the hollow tube to enhance a more precise positioning of the electrodes to maximize the recording of ECG information from a subject. This electrode harness requires a downward biased weight of the electrode carrying tube to enhance the attachment and therefore signal from the electrode. Finally, another example is described in U.S. Pat. No. 6,611,705 to Hopman et al.

Hopman et al. describes the use of an ECG electrode connector with a plurality of expandable arms interconnected with the electrodes and each of the expandable arms having releasable connectors.

The electrode harnesses that have been developed suffer from one or more of the following drawbacks. None of the electrode harnesses developed use standard gel type electrodes, wherein once attached or connected, the electrodes cannot be released. Therefore, once used with these connectable electrodes the existing electrode harnesses cannot be disposed of in one piece along with the harness since the electrode may become separated from the harness. Another drawback is none of the electrode harnesses contain an adjustable connection point for the electrodes to allow for the harness to be adapted to either different sized subjects or different applications. Still another drawback is none of the electrode harnesses electrically shield the electrodes from large defibrillator voltages. Still yet another drawback is that none of the electrode harnesses contains trimable electrodes or electrical connections so the electrode harness can be personally modified for a particular subject or application. Finally, none of the electrode harnesses contain a dry electrode, which can be used to enhance reduce the complexity, and variability of the measurement system and the electrode site preparation prior to application. "Dry" electrodes require no skin preparation or conductive gel. (with adhesive and without adhesives contained on the harness/ and electrode)

In view of the foregoing drawbacks, it is the object of the present invention to develop an electrode harness, which overcomes one or more of these drawbacks. More specifically, it would be desirable to have an electrode harness with non-releasable connectors. Additionally, it is the object of the present invention to develop an electrode harness with an adjustable electrode connection point. Further, it is the object of the present invention to have an electrode harness which is shielded from large defibrillator voltages. Still further, it is the object of the present invention to develop an electrode harness that contains trimable electrodes or electrical connections. Finally, it is the object of the present invention to have an electrode harness containing dry electrodes.

SUMMARY OF THE INVENTION

The present invention relates to an electrode harness and more particularly to an electrode harness with various features, which enhance the use and performance of the electrode harness. The present invention further relates to a method of taking biopotential measurements.

The electrode harness' and methods of the present invention allow for use with most applications where biopotential measurements are taken. The electrode harness' can be used in ECG (or EKG), EEG, EMG, and other such biopotential measurement applications. Because of the versatility of various embodiments of the present invention, preferably the electrode harness can be adjusted for different applications or for application to various sized and shaped subjects. The electrode harness is further preferably part of a system, which includes either wireless or tethered bridges between the electrode harness and a monitor, and preferably includes various forms of processors for analyzing the biopotential signal.

The electrode harness of the present invention overcomes one or more of the significant drawbacks of other electrode systems. One of the features of various embodiments of the present invention includes a harness with lockable or non-releasable connectors, which allows for disposal or removal of the electrode harness and electrodes in one piece (application of harness and electrodes while maintaining the connection: i.e doesn't fall off or lose electrical connect once inserted. This prevents clutter and more importantly medical waste by reducing the possibility that the electrodes separate from the harness. Another feature of the electrode harness of the present invention is the use of an adjustable. connection point. More specifically, the electrode harness is provided with an electrode, which can be positioned in various locations over one of the arms of the harness allow for more accurate/reliable data capture. Preferably, the electrode operates on a track incorporated into the electrode harness over which the electrode can be moved and operated. Still another feature of the electrode harness of various embodiments of the present invention is partial or full shielding of the electrical pathways of the harness from electrical noise or more importantly from large defibrillator voltages. Still another feature of various embodiments of the electrode harness of the present invention is the ability to trim electrodes, electrical connections and/or arms of the electrode harness. Finally, another significant feature of the electrode harness of various embodiments of the present invention is the use of an electrode harness containing one or more dry electrodes.

In one embodiment, the present invention includes an electrode harness for physiological monitoring of a subject, the electrode harness comprising material operable to interconnect at least two electrodes; and at least two electrode connectors provided on the material wherein the at least two electrode connectors are non-releasable connectors.

In another embodiment, the present invention includes an electrode harness for physiological monitoring of a Human (infant through adult) or animal subject, the electrode harness comprising at least two electrodes; and material operable to interconnect the at least two electrodes; wherein the material comprises at least two expandable arms, each of the at least two arms corresponding to the at least two electrodes which are permanently attached to the at least two expandable arms. What about 1 or more expandable arms i.e SLINKY with electrode on either end In still another embodiment, the present invention includes an electrode harness for physiological monitoring of a subject, the electrode harness comprising at least two dry electrodes; and material operable to interconnect the at least two dry electrodes; wherein the at least two dry electrodes are permanently attached to the material.

In still another embodiment, the present invention includes an electrode harness for physiological monitoring of a subject, the electrode harness comprising at least two dry electrodes each with a releasable connector; and material operable to interconnect the at least two dry electrodes with at least two mating connectors for the corresponding releasable connectors.

In still another embodiment, the present invention includes an electrode harness for physiological monitoring of a subject, the electrode harness comprising at least two dry electrodes; material operable to interconnect the at least two dry electrodes; and at least two corresponding non-releasable connectors connected to the material.

In still another embodiment, the present invention includes an electrode harness for physiological monitoring of a subject, the electrode harness comprising at least one electrode with adjustable connector; and a material operable to interconnect at least two electrodes; and a track system attached or integral to the material wherein the at least one electrode is movable along the track system with the adjustable connector.

In still another embodiment, the present invention includes an electrode harness for physiological monitoring of a subject, the electrode harness comprising at least two electrodes; and a material operable to interconnect the at least two electrodes wherein the material is trimable to remove one of the at least two electrodes.

In still another embodiment, the present invention includes an electrode harness for physiological monitoring of a subject, the electrode harness comprising at least two electrodes; and a material operable to interconnect the at least two electrodes, the material comprising at least two electrical pathways from the at least two electrodes, the electrical pathway being electrically shielded from large defibrillator voltages.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

DESCRIPTION OF THE PREFERRED EMBODIMENTS

Figure 1:
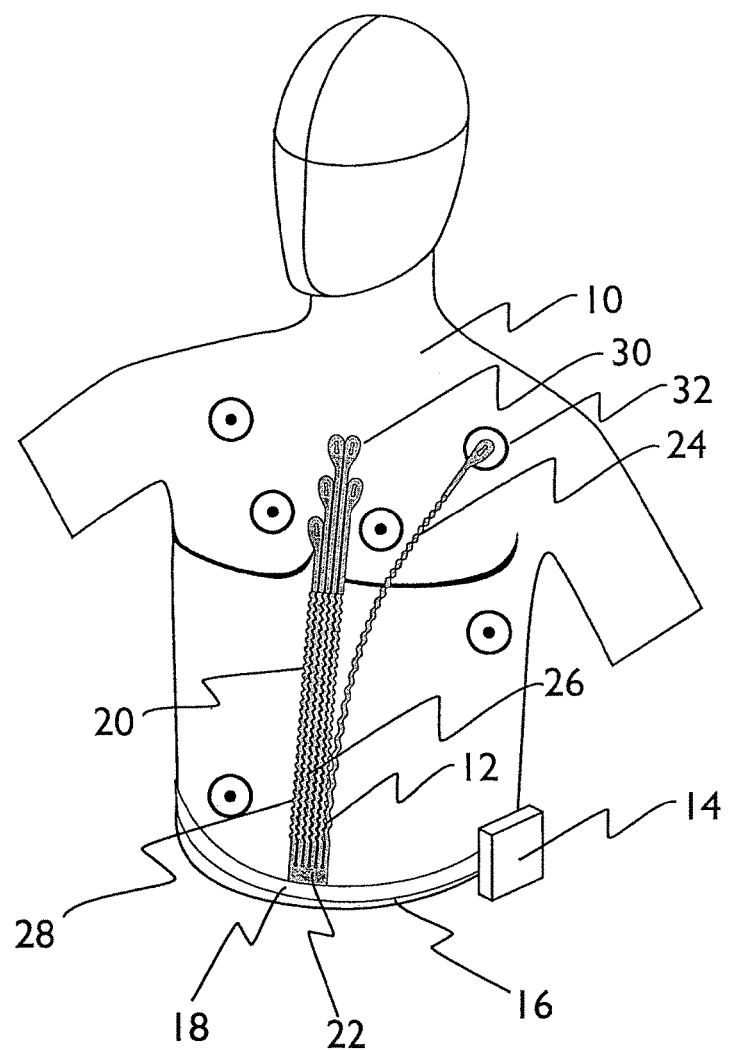
FIG. 1. Schematic view of a subject wearing a biopotential measurement system with one embodiment of the electrode harness of the present invention.

The present invention relates to an electrode harness and more particularly to an electrode harness with various features, which enhance the use and performance of the electrode harness. The present invention further relates to a method of taking a physiological or preferably a biopotential measurement.

The various embodiments of the electrode harness and methods of the present invention allow for use with most applications where biopotential or physiological measurements are taken: The electrode harness of the present invention is preferably used for sensing or detecting a physiological or biopotential signal from a subject. The subject from which a physiological signal is measured being a human or other form of animal. The electrode harness can be used in a variety of applications including but not limited to electrocardiography (ECG), electroencephalography (EEG), electrical impedance tomography (EIT), electromyography (EMG), electro-oculography (EOG) and Bio-electrical impedance (BIA), biopotential or physiological measurement applications. Because of the versatility of various embodiments of the present invention, preferably the electrode harness can be adjusted for different applications or for application to various sized and shaped subjects. The electrode harness is further preferably part of a system, which includes either wireless or tethered bridges between the electrode harness and a monitor, and preferably includes various forms of processors for analyzing the biopotential signal. The electrode harness of the present invention further allows for greater improvement in home health care monitoring systems.

The electrode harness of the present invention preferably comprises a material operable to interconnect at least two electrodes. More preferably, the material is formed from a multi-layer laminate. The material of the electrode harness of the present invention interconnects at least two electrodes by preferably providing separate electrical pathways to each of the electrodes. These materials can be processed by any means known to those skilled in the art. Preferable methods include silk screening or photo-resist processes where electrical traces are formed on or incorporated in various layers of the laminate.

Once the appropriate electrical pathways or traces are formed on one or more layers for use in the material of the present invention, the multi-layer laminates can be formed by any of the traditional coating and conversion processes known to those skilled in the art. Preferably, the conductive layers are joined with other layers of adhesive, coatings, facestocks and liners to provide a multi-layer laminate with the appropriate features and/or properties necessary for the specific application of the electrode harness. The multi-layer laminates then are preferably die cut and/or formed into the desired shapes for these applications. One example is to provide for a shape, which allows the material or arms formed from the material to expand or adjust to different subject sizes or body placement locations.

Another example is the formation during the conversion process of a mechanical weak point in the material. The mechanical weak point can take many forms. Preferably, the mechanical weak point is a perforation through the material or a scoring of the surface of the material. The mechanical weak point is one preferred feature that allows for a later change in the configuration of the electrode harness. Thus, separating the electrical pathways and/or electrode leads or arms from one another by use of the mechanical weak point, allows for a wider area for which to place the electrodes. Such configurations enabled by the mechanical weaknesses would be greater in area then configurations allowable when the electrical pathways are permanently configured. Separation of the electrical pathways from one another in order to more accurately place individual electrodes on the skin of the monitored subject allows for a wider variety of uses from the same electrode harness. The force required to separate the mechanical weak points in the substrate should be greater than forces normally occurring during use of the electrode harness. In one embodiment, the mechanical weak point extends from the electrode connector down through the entirety of the electrical pathway, terminating at the transmitter plug.

In another embodiment, mechanical weak points are created laterally across the electrode harness. Lateral mechanical weak points, similarly to the longitudinal mechanical weak points, are made in the substrate material and not in the electrical pathways themselves. Mechanical weak points across the harness allow for the electrode harness including the electrical pathways to be severed, thus shortening their length. Any number of lateral mechanical weak points can be made at any interval along the electrode harness.

Another embodiment of the invention contains a track system for placement of electrodes. This track system operates in order for the user to place electrodes at any point along the electrical pathway. The electrical pathway is embedded in the substrate. Above the entire length of the electrical pathway is a slit in the substrate that allows the user to electrically connect an electrode connector to the electrical pathway. The slit substantially covers the electrical pathway, protecting it from outside signals or unwanted physical contamination. The electrode connector electrically connects to the electrical pathway via a conductive pin or protrusion that when attached to the flexible substrate, passes through the slit in the flexible substrate and rests in contact with the electrical pathway. The conductive pin therefore creates a pathway for biopotential signals received by the electrode to be transmitted through the conductive pin to the electrical pathway in the electrode harness. In another configuration, the electrical pathway is completely covered by the flexible substrate. However, the substrate is perforated above the electrical pathway allowing the conductive pin on the electrode connector to puncture the perforations and electrically connect the electrode to the electrical pathway embedded in the substrate. This configuration has the advantage of additional protection for the electrical pathway embedded in the substrate.

In still another embodiment, the electrical pathways are electrically shielded from large defibrillator voltages and smaller voltages, both which would degrade the biopotential signal. The electrical pathways within the flexible substrate are longitudinally enclosed with a conductive layer of shielding, such as metal or foil, extending from the electrode connector to the output plug at the opposite end of the electrode harness. Each individual electrical pathway is shielded.

The material of the electrode harness of the present invention, which is operable to interconnect the electrodes preferably, comprises electrode connectors to mechanically and electrically connect the electrode harness with various types of electrodes. The electrical connectors can be releasable, lockable, non-releasable or permanent connections. Releasable connectors are those connectors to which electrodes can be connected or disconnected with little or no effort. Traditional button type gel-electrodes use such connectors. The drawback of these types of connectors is that sometimes they become inadvertently disconnected through motion of the subject or by external forces on the materials or leads attached to such connectors. In addition, like the disposable or single use electrodes, the electrode harness may also be designed or intended to be for one use only. However, if releasable connectors were to be used, the end user may inadvertently make use of the electrode harness multiple times thereby undermining the intended performance of the harness. Lockable connectors are connectors that can be removed from the electrode but only upon the application of forces greater than those normally encountered during the application for which the connector is being used or where there is some mechanical mechanism, which needs to be activated or opened in order to release the electrode. Non-releasable connectors are those connectors, which after attaching to an electrode do not release the electrode unless the connector is somehow destroyed. Permanent connections are where the electrode is glued, welded, brazed or permanently attached by some means to the material of the electrode harness. Where connectors are used, the connectors may comprise clips, snaps, and both male and female connectors. The connectors may also include any other device for mechanically and electrically connecting the electrode to the electrode harness. Where the electrode harness has various arms, those arms may include one or more electrodes.

The electrodes used with the electrode harness and methods of the present invention include but are not limited to gel-type electrodes, dry electrodes, implantable electrodes, and the like. The gel-type electrodes and implantable electrodes are known to those skilled in the art. The gel-type electrodes usually comprise a sensing element and a conductive gel for transmitting the signal between the subject's skin and the sensing element. Most preferably, however, dry electrodes are used. The dry electrodes comprising a penetrator for detecting physiological signals below the surface of the skin as a sensing element. Dry physiological recording electrodes of the type described in U.S. patent application Ser. No. 09/949,055, which issued into U.S. Pat. No. 6,782,283 on Aug. 24, 2004 are herein incorporated by reference. Dry electrodes provide the advantage that there is no gel to dry out, no skin to abrade or clean, and that the electrode may be applied in hairy areas such as on an animal or on a male human's chest. Alternatively, the subject(s) skin may be mechanically abraded, or an amplified electrode may be used. Preferably, the at least two electrodes are one signal electrode and one reference electrode. The at least two electrodes don't have to be of the same type, i.e., for example one could be a conductive gel electrode and the other a dry electrode. The at least two electrodes can be any shape known to be useful to those skilled in the art. For example the electrodes can be circular or non-circular in shape.

The expandable arm(s) of the present invention in various embodiments preferably comprises memoryless material, such as materials discussed herein. The expandable arm is die cut or shaped into different types of patterns, which allow the arm to be adjusted. Two such shapes are an accordion or a serpentine pattern. When expanded, a portion or all of the expandable arm is extended. Where only a portion of the expandable arm is extended, another portion remains folded or unbroken, or only partially unfolded or broken. Pressure on the electrode from the material of the electrode harness or arms of the electrode harness is preferably avoided, providing for a more stable connection of the electrode to the subject. The expandable arm allows for extension as needed without extra extension and resulting loose material to be tangled or which provides discomfort to the subject. In alternative embodiments, a stretchable or elastic expandable arm is used. In yet other embodiments, a non-expandable arm is used. In still yet other embodiments, various combinations of these features are used. In further preferred embodiments, the electrode harness or the arms themselves comprise spooling or other mechanisms to allow for retraction or expansion of the arms.

The electrode harness of the present invention is preferably connected to a tether or a wireless transmitter or transceiver by a lead connector. A lead connector functions to connect the electrical pathways or traces from the material of the electrode harness into the tether or wireless system via a standard electrical configuration. The tether is a wired connector to connect the electrode harness to a monitor, processor or other devices, which preferably enables the subject or their health care provider to utilize the biopotential signals. The transmitter or transceiver receives the signals from the electrodes, and comprises a radio, ultrasound, infrared or other transmitter. Preferably, the transceiver operates according to Bluetooth specifications or communications/electronics specifications, i.e., FCC. The transmitter or transceiver can include but are not limited to various components such as electrode signal channels, a multiplexer, analog to digital converter(s), a controller, a radio, a battery, and the like. Additional, fewer or different components can be used. Adaptable to any biopotential capture system In one embodiment, the transmitter is operable to minimize introducing undesired noise or signals. The selected signals are transmitted as radio or other signals modulated with a carrier signal. Various formats can be used for transmission of signals. Such formats include, but are not limited to Bluetooth, TCP/IP, or other formats. The controller controls the signal acquisition and signals. The transmitted signals comprise data representing the biopotential signals received from the electrodes. In alternative embodiments, the controller may also process prior to transmission so that the signals comprise vector data. In one embodiment, the transmitter also receives control information from the receiver, such as instructions to resend signals.

The transmitter is positioned near, or attached to, the monitored subject. The transmitter may be positioned on the hub, expandable arm, arm juncture, or other position where it may receive signals from the electrodes. The receiver may be attached to the monitored subject through the use of an appendage band (e.g. arm, leg, wrist, ankle, etc.). The transmitter is provided with a pocket, surface, or belt mount. In alternative embodiments the transmitter can be placed in a pocket of clothing, elsewhere on the subject, or in close proximity to the subject.

In one embodiment, the transmitter is removable from the electrical pathway leading to the electrodes. Clips, plugs, clips, screws, bolts, latches, adhesive, or other devices may be used to releasably connect the transmitter to the electrical pathway. Electrical contact is provided by connectors operable to withstand electrical energy produced by a defibrillator. These connectors may also provide the physical connection between the transmitter and the electrical pathways mentioned above. The transmitter is removed for recharging the battery, and/or there is a mechanism such as a plug used to recharge the battery without removal. The battery or transmitter like the electrode harness and the electrodes can be used for multiple days or multiple times and is separately disposable to avoid costly replacement of the entire system. The receiver comprises a radio, infrared, ultrasound or other receiver. An application specific integrated circuit, digital signal processor or other circuit for receiving signals from the transmitter, decoding the received signals, and generating representative electrode signals is used. In one embodiment, the receiver comprises a transceiver for two-way communication with the transmitter. For example, a transceiver operable pursuant to the Bluetooth specification is provided.

The radio demodulates the received signals for identifying digital data representing the combined electrode signals. In various embodiments, the radio also includes a modulator for transmitting control information. The controller controls operation of the various components and may further process the signals from the radio, such as interpolating data, converting the signals to digital information, generating control signals for the transmitter, operating any user interface, operating any user output or input devices, and diagnosing operation of the system. Preferably, the controller in the receiver interpolates the electrode signals to return the effective sample rate to about 3 kHz or another frequency. This enables the reconstruction filters to have a cutoff frequency many times the bandwidth of the electrode signals, thus minimizing any differences in group delay at the frequencies of interest.

With the wireless biopotential monitoring system, the wires from a standard biopotential monitor (e.g. ECG, EEG, etc.) are attached to the connectors on the wireless receiver. The wires comprise a lead-wire set, cable or electrode connectors from or for the biopotential monitor. The posts are labeled as electrodes and the wires are connected with corresponding outputs on the receiver. The receiver outputs signals as if from the corresponding electrodes for processing by the biopotential monitor. In alternative embodiments, the receiver includes wires for connecting with the biopotential monitor.

The biopotential monitor comprises one or more of a bedside monitor, a transport monitor or a discrete (i.e. diagnostic) monitor. Bedside and transport monitors are used for continuous monitoring, such as associated with hexaxial-lead monitoring. A discrete monitor typically is used periodically for analysis, such as associated with "12-lead" monitoring or obtaining multiple vectors associated with precordial and/or hexaxial leads. The monitor processes the electrode signals as if the signals were received directly (hard-wired or tethered) from the electrodes. Neither the transmitter or receiver includes differential amplifiers for determining a heart vector associated with two electrodes.

Some monitors test for failure or malfunction of electrodes. For example, a signal is output on the lead wire to the electrode or a direct current level associated with the signal from which the electrode is monitored. To continue to provide this functionality, the wireless biopotential system tests for electrode failure or malfunction and indicates the results to the monitor. For example, the transmitter performs the same or similar tests as the monitor. In other embodiments, the transmitter or receiver determines whether the biopotential signal is within an expected range. For example, the controller compares the digital electrode signals, such as after interpolation, to maximum and minimum thresholds. If either threshold is exceeded by a particular number of samples or for a particular time, a lead-off or faulty electrode is indicated. When one or more samples are subsequently within hysteresis limits of the thresholds, then an error is no longer indicated. When a lead-off condition is indicated, the receiver opens an analog switch, or alternatively, does not generate a signal for the output corresponding to the malfunctioning or failed electrode. As a result, the monitor indicates a failure of the electrode. If the transmitter and receiver are out of radio communication range, a lead-off condition is presented to the monitor.

FIG. 1 shows a schematic view of a subject wearing a biopotential measurement system with one embodiment of the electrode harness of the present invention. In FIG. 1, the subject 10 is wearing a biopotential measurement system 12. This particular embodiment of the biopotential measurement system 12 comprises a transceiver 14, which is worn by the subject 10 about the waist 16 by a belt 18. An electrode harness 20 is mechanically connected to the belt 18 via a connector 22. The electrode harness 20 is further electrically connected via the same connector 22 to the belt 18. The belt 18 comprises electrical pathways (not shown), which carry the biopotential signals to the transceiver 14.

In this embodiment, the electrode harness 20 comprises multiple electrical pathways (not shown) for each of the multiple expandable arms 24. In this particular embodiment there are six expandable arms 24. The material 26 of the electrode harness 20 having one or more mechanical weak points 28 for separation of one or more expandable arms 24 from the body of the electrode harness 20 or material 26. Each of the expandable arms 24 comprising a lockable connector 30, which can be used to both mechanically and electrically attach to the electrode 32. The expandable arms 24 and the ability to separate one or more of them from the body of the electrode harness 20 allowing for the positioning and connection of electrodes 32 in various configurations on a variety of subjects 10.

Figure 2A:
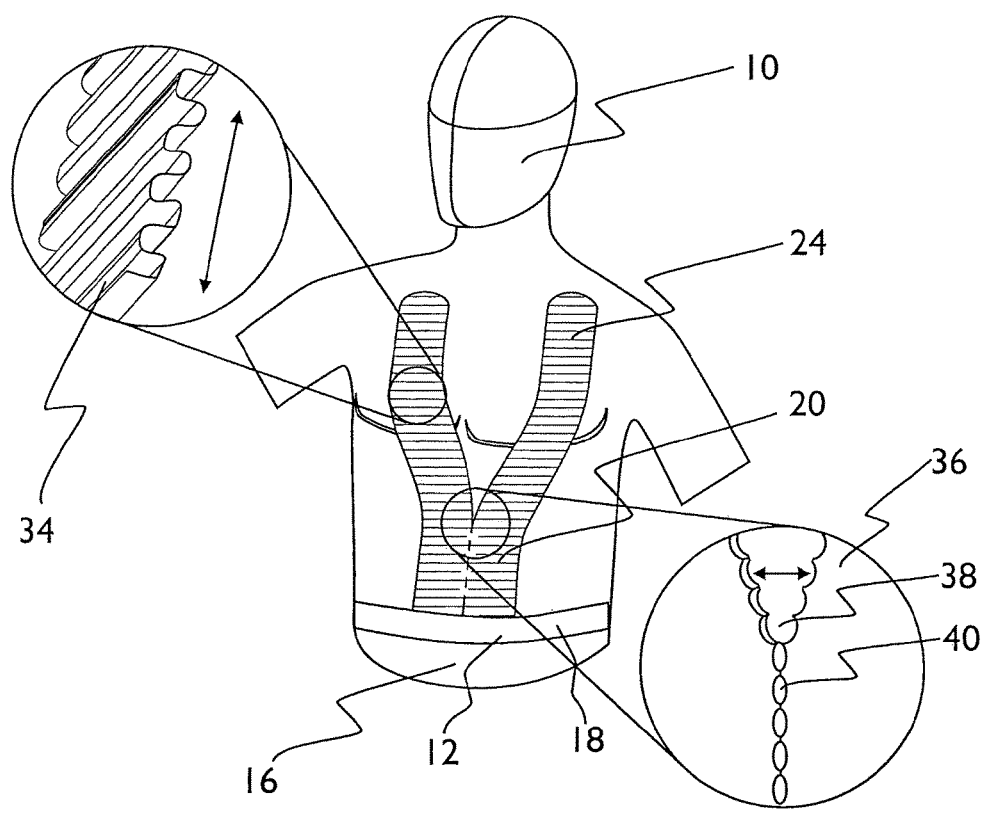
FIG. 2. *a*) Schematic view of a subject wearing a biopotential measurement system with another embodiment of the electrode harness of the present invention, and *b*) the electrode harness of FIG. 2 *a*).
Figure 2B:
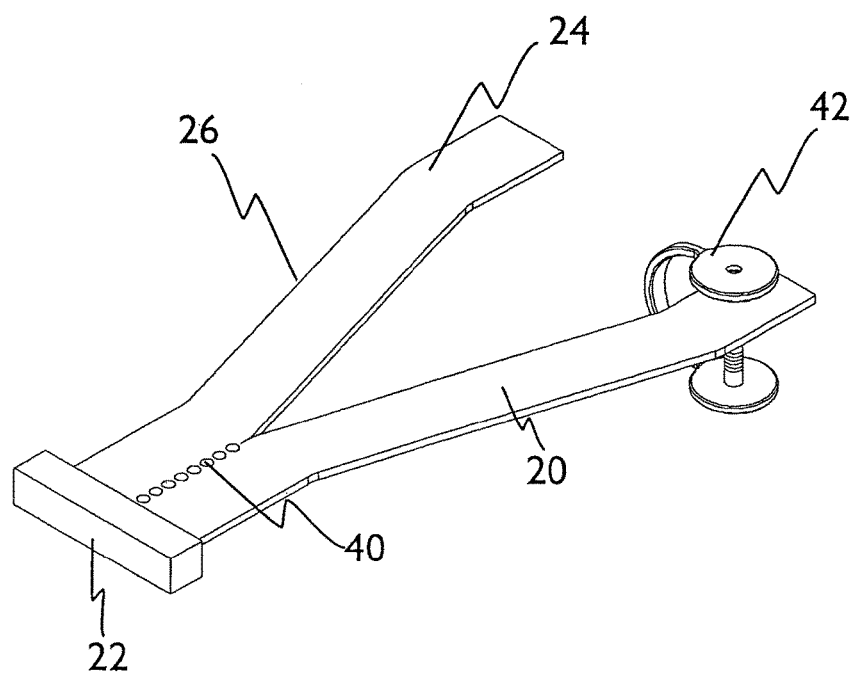

FIG. 2 shows a schematic view of a subject wearing a biopotential measurement system with another embodiment of the electrode harness of the present invention, and the electrode harness of this particular embodiment in more detail. In FIG. 2 a), the subject 10 is wearing a biopotential measurement system 12. This particular embodiment of the biopotential measurement system 12 comprises a transceiver (not shown), which is worn by the subject 10 about the waist 16 by a belt 18. An electrode harness 20 is mechanically connected to the belt 18 via a connector 22. The electrode harness 20 is further electrically connected via a connector (not shown) to the belt 18. The belt 18 comprises electrical pathways (not shown), which carry the biopotential signals to the transceiver (not shown). The electrode harness 20 comprises at least two expandable arms 244 In this embodiment, the arms 24 are expandable through the use of both flexible materials and the use of accordion type features 34 in the materials to allow users to expand the arms 24 for better positioning. The electrode harness 20 further comprises a mechanical weak point 36 shown in the call out. The mechanical weak point 36 is in the form of perforations 40, which allow the harness material to be torn 38 allowing for better positioning of the harness 20.

FIG. 2 b) is a perspective view of the electrode harness 20 in FIG. 2 a). In FIG. 2 b) the electrode harness 20 comprises two arms 24. The material 26 of the electrode harness 20 having one or more mechanical weak points or perforations 40 for separation of one or more expandable arms 24 from the body of the electrode harness 20 or material 26. Each of the expandable arms 24 comprising a non-releasable connector 42, which can be used to both mechanically and electrically attach an electrode or connector/electrode combination 42. The electrode harness 20 further comprising a connector 22 for mechanically and electrically connecting the electrode harness 20 with the rest of the system (not shown).

Figure 3:
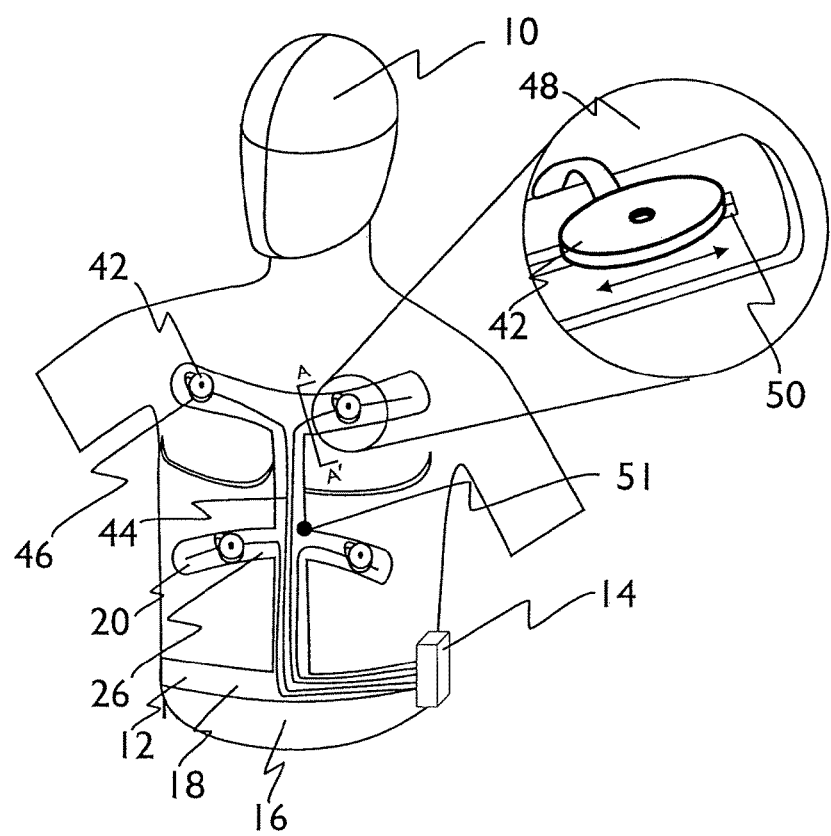
FIG. 3. Schematic view of a subject wearing a biopotential measurement system with still another embodiment of the electrode harness of the present invention.

FIG. 3 shows a schematic view of a subject wearing a biopotential measurement system with still another embodiment of the electrode harness of the present invention. In FIG. 3, the subject 10 is wearing a biopotential measurement system 12. This particular embodiment of the biopotential measurement system 12 comprises a transceiver 14, which is worn by the subject 10 about the waist 16 by a belt 18. The electrode harness 20 is further comprises a belt 18 for securing the electrode harness 20 to the subject 10. The electrode harness 20 and belt 18 combination comprises electrical pathways 44, which carry the biopotential signals to the transceiver 14. In this embodiment, the electrode harness 20 comprises multiple electrical pathways 44 for each of the multiple arms 46. In this particular embodiment there are four arms 46. Each of the arms 46 comprising a non-releasable connector 42, which can be used to both mechanically and electrically attach to the electrode (not shown). This electrode harness 20 also containing a track system shown in call out 48. The track system comprising a track 50 over which the connector 42 can be moved to mechanically and electrically connect the electrode (not shown) for proper positioning on the subject 10. The electrode harness 20 also comprising a marker 51 which can be used to line up the harness with an anatomical feature of the subject 10 such as for example the tip of the sternum or some other marker placed on the subject 10. Call out 43 shows the marker 51 as well as a weakness 45 in the material to allow for removal of an electrode 42. The box housing the transceiver 14 also optionally can further comprise a monitor which tests for electrode failure or malfunction.

Figure 4:
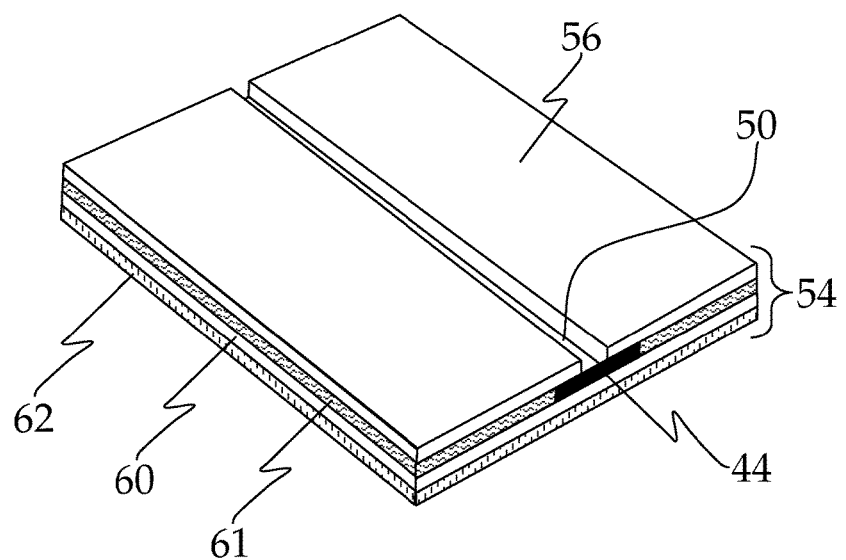
FIG. 4. Perspective view of a section from the electrode harness of FIG. 3 cut along the line A-A' of one embodiment of the laminate material for the track system in FIG. 3, and which further provides for electrical shielding of the electrical pathways of the electrode harness.

FIG. 4 shows a perspective view of a section from the electrode harness of FIG. 3 cut along the line A-A' of one embodiment of the laminate material 54 for the track system in FIG. 3. This laminate material 54 further provides for electrical shielding of the electrical pathways 44 of the electrode harness. The laminate material 54 in this particular embodiment comprises four distinct layers. Those being top 56 layer, shielding layer 61 protective layer 60 and an adhesive layer 62. The top 56 and other layers 60, 61, 62 forming a track 50 over which the electrode connector (not shown) can be moved and positioned. While the shielding layer 61 is shown in this embodiment as being positioned on either side of the electrical pathway 44, it will be understood that in other embodiments the shielding layer may be arranged so as to longitudinally enclose the electrical pathway 44 with a conductive layer of shielding as noted in the specification above. The shielding layer 61 is beneficial as it can be used to prevent electrical interference with the biopotential signal and/or to prevent large stray currents from damaging the system or harming the subject.

Figure 5:
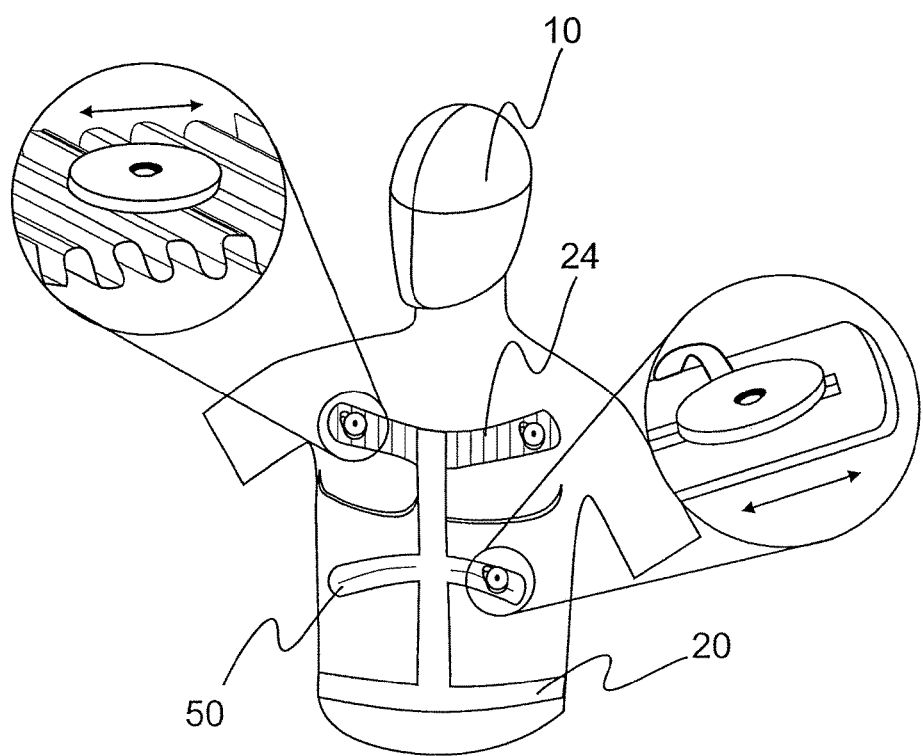
FIG. 5. Schematic view of a subject wearing a biopotential measurement system with still another embodiment of the electrode harness of the present invention.

FIG. 5 shows a schematic view of a subject wearing a biopotential measurement system with still another embodiment of the electrode harness of the present invention. In FIG. 5, the subject 10 is wearing an electrode harness 20. The electrode harness 20 in this embodiment comprises two expandable arms 24 and two arms containing a track system 50.

Figure 6A:
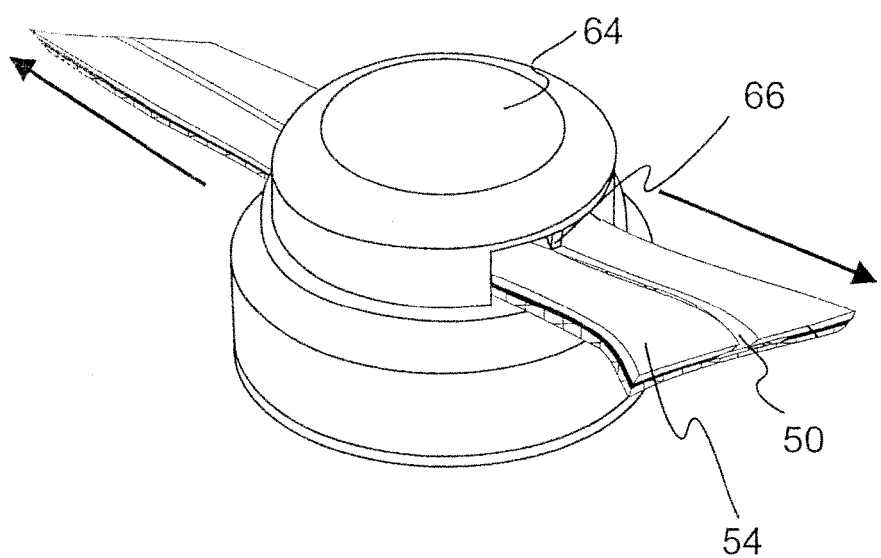
FIG. 6. *a*) Perspective view of one embodiment of a track electrode on the track of certain embodiments of the electrode harness of the present invention, and *b*) a cross-sectional view of such track electrode on the track of such electrode harness.
Figure 6B:
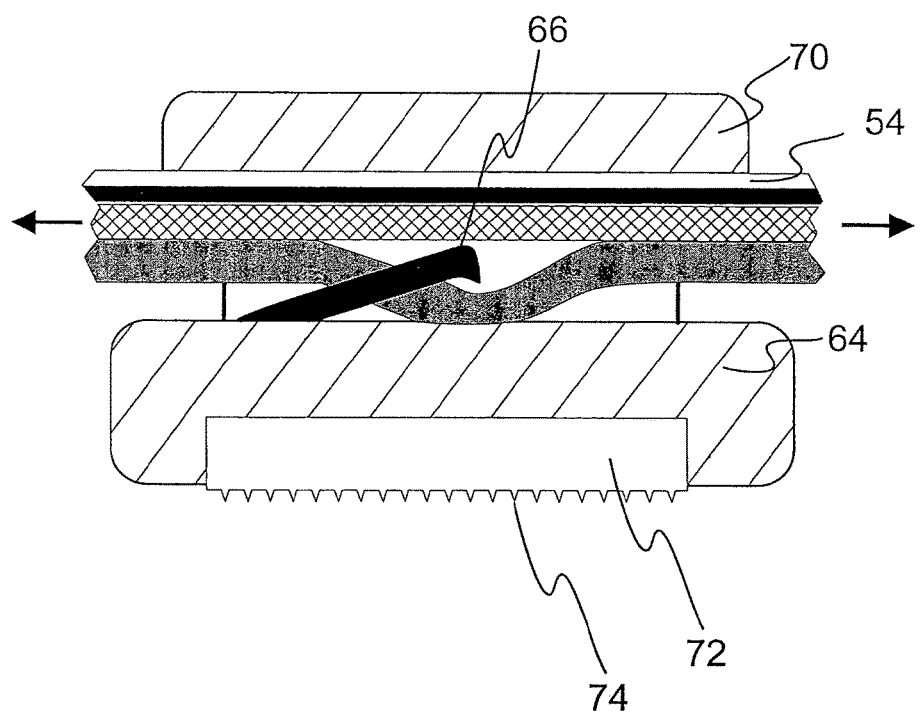

FIG. 6 a) shows a perspective view of one embodiment of a track electrode on the track of certain embodiments of the electrode harness of the present invention, and b) a cross-sectional view of another embodiment of a track electrode on the track of such electrode harness. In FIG. 6 a) the track electrode 64 is moveable along the track 50 formed by the laminate 54. The track electrode 64 further has a spring-type connector 66, which moves with the electrode 64 along the track 50 and keeps the electrode 64 connected with the electrical pathway within the laminate material 54. The cross-sectional view in FIG. 6 b) shows the injection molded case 70 of another embodiment of a track electrode 64, the spring connector 66, and a dry penetrating electrode 72. The dry penetrating electrode 72 comprising at least one penetrator 74 for picking up biopotential signals in the epidermis of a subject's skin.

Figure 7:
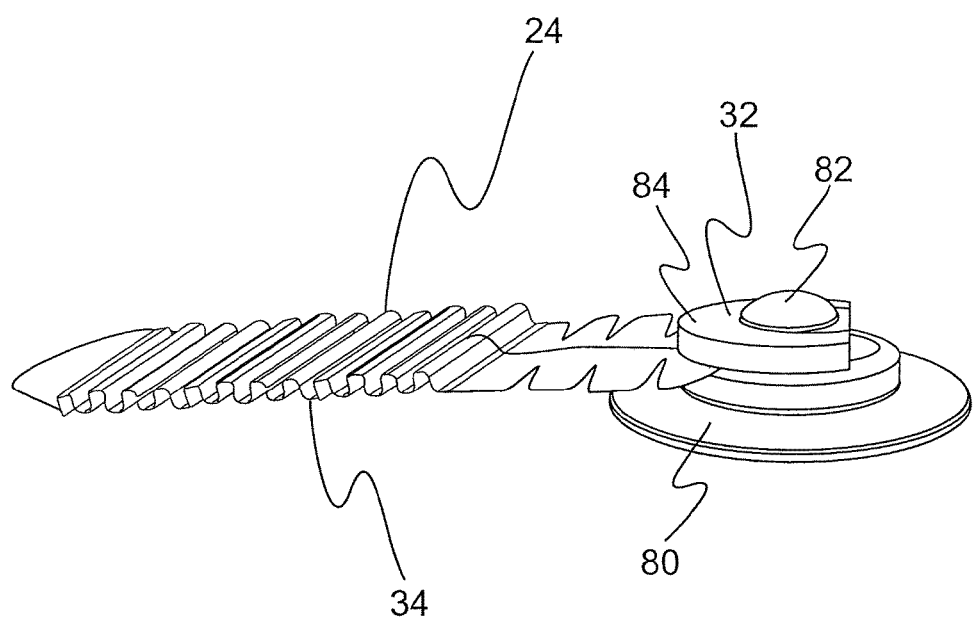
FIG. 7. Perspective view of one embodiment of an expandable arm of certain embodiments of the electrode harness of the present invention.

FIG. 7 shows a perspective view of one embodiment of an expandable arm of certain embodiments of the electrode harness of the present invention. The expandable arm 24 in FIG. 7 is expandable through the use of both flexible materials and the use of accordion type features 34. The expandable arm 24 has a lockable connector 32, which clips snugly about the button 82 of a conventional type gel electrode 80. The expandable arm 24 can be used to better position the electrode 80 on the subject (not shown).

Figure 8:
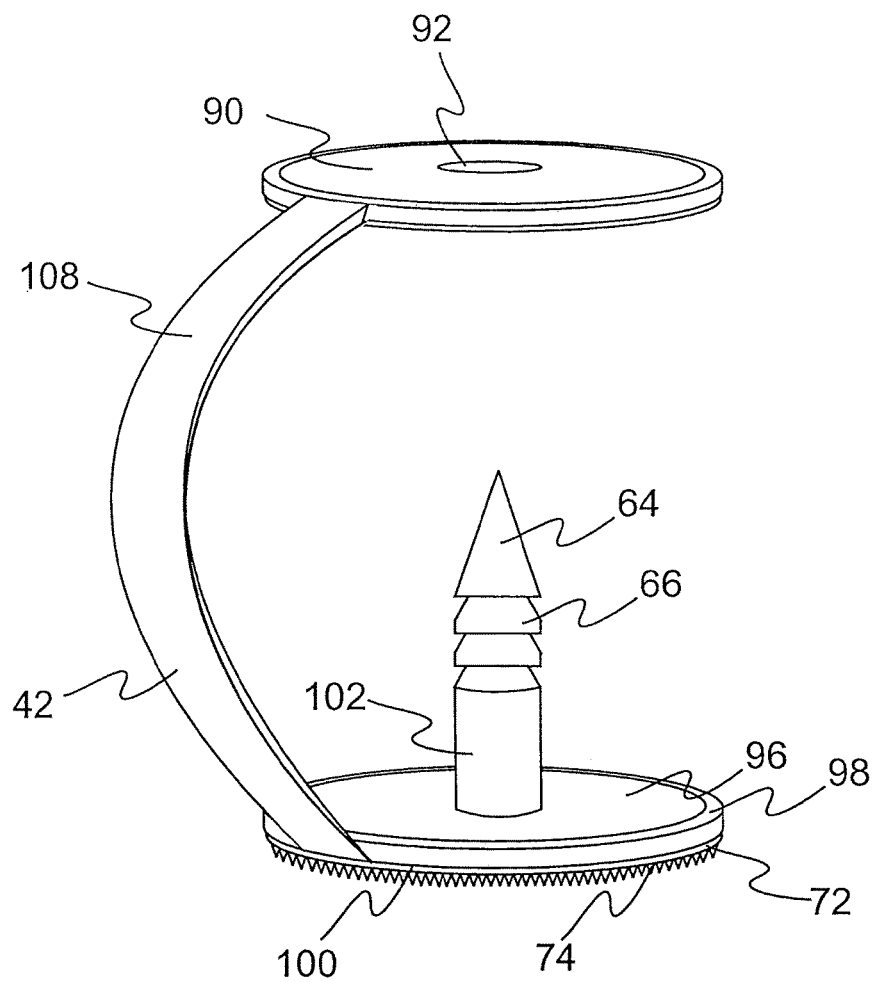
FIG. 8. Perspective view of a non-releasable connector and electrode used in various embodiments of the present invention.

FIG. 8 shows a perspective view of a non-releasable connector and electrode used in various embodiments of the present invention. The non-releasable connector 42 in FIG. 8 comprises a top member 90 with a female orifice 92 and a bottom member 96 having an upper 98 and a lower surface 100. The upper surface 98 having a male locking stud 102 protruding from the upper surface 98. The male locking stud 102 having a sharpened penetrator 64 for piercing the electrode harness (not shown) and locking ribs 66 to prevent release of the connector 42 from the electrode harness (not shown). The top 90 and bottom 96 members being attached by a connecting bridge 108. The lower surface 100 of the bottom member 96 comprising a dry electrode 72 with at least one penetrator 74.

Figure 9A:
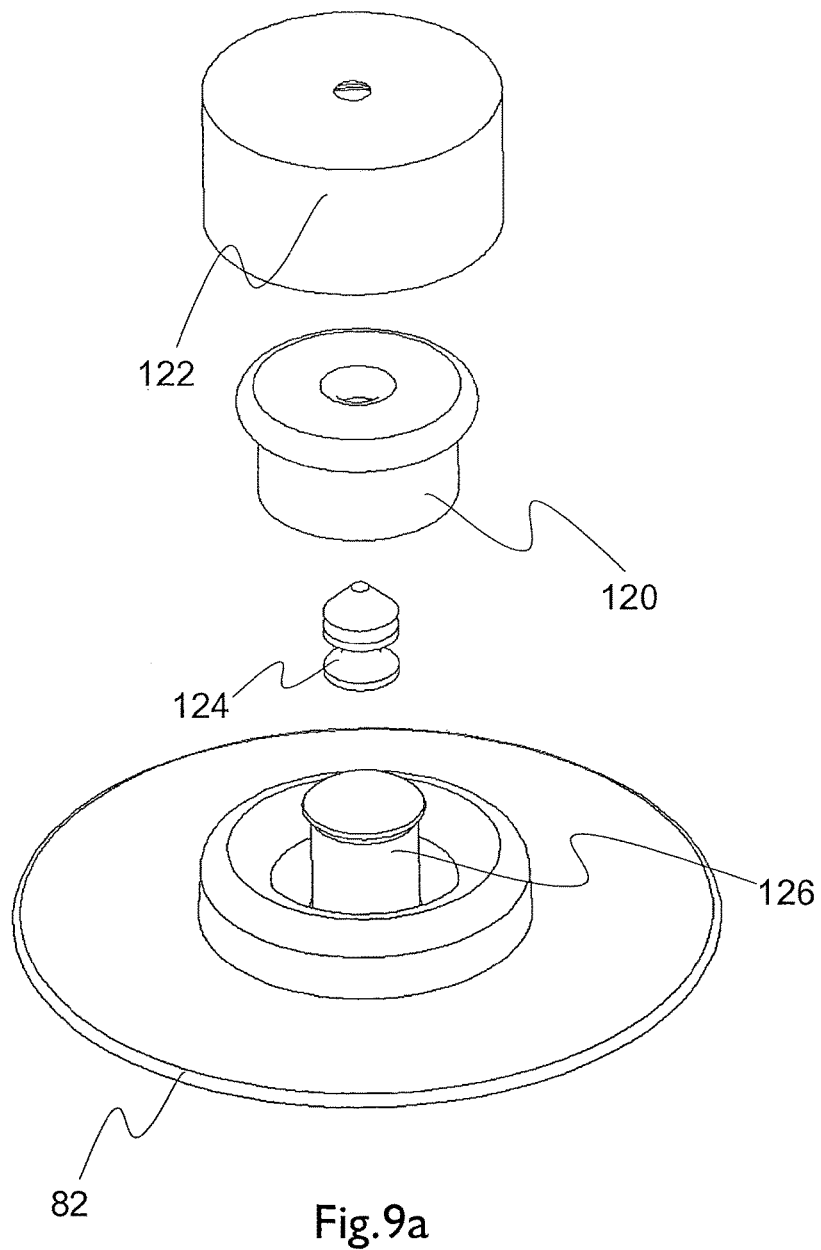
FIG. 9. a) Exploded view of another embodiment of a non-releasable connector used in various embodiments of the present invention, and b) a cross-sectional view of the same.
Figure 9B:
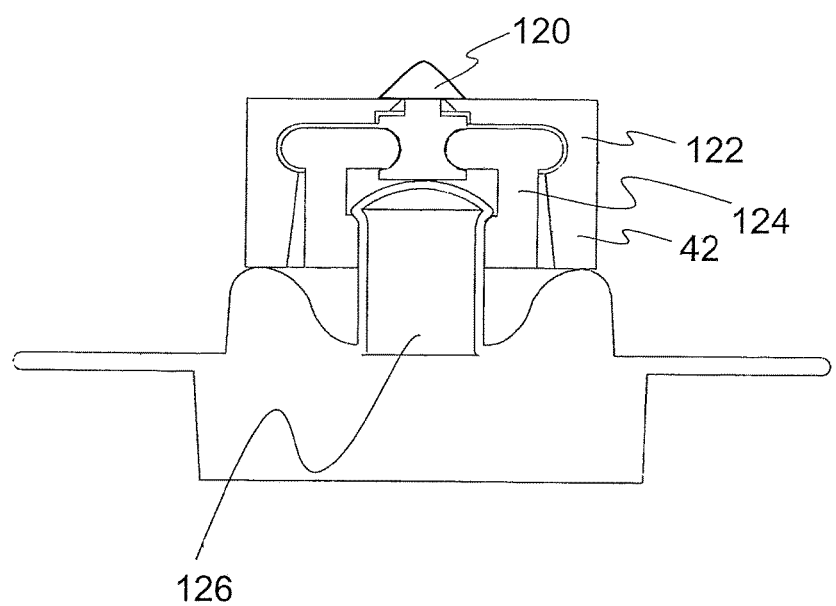

FIG. 9 shows an exploded view of another embodiment of a non-releasable connector used in various embodiments of the present invention, and a cross-sectional view of the same. The non-releasable connector shown in FIGS. 9 a) and b) comprises a lever 120, a shell 122, and a cantilever 124. FIG. 9 a) also shows the button connector 82 of a typical gel-type electrode (not shown). The button connector 82 further comprises a stud 126. When the connector 42 is applied over the stud 126 of the button connector 82, the lever 120 is forced up through the shell 122 and cantilever 124 causing the button connector 82 to be in electrical connection and locked into place by the connector 42.

Figure 10:
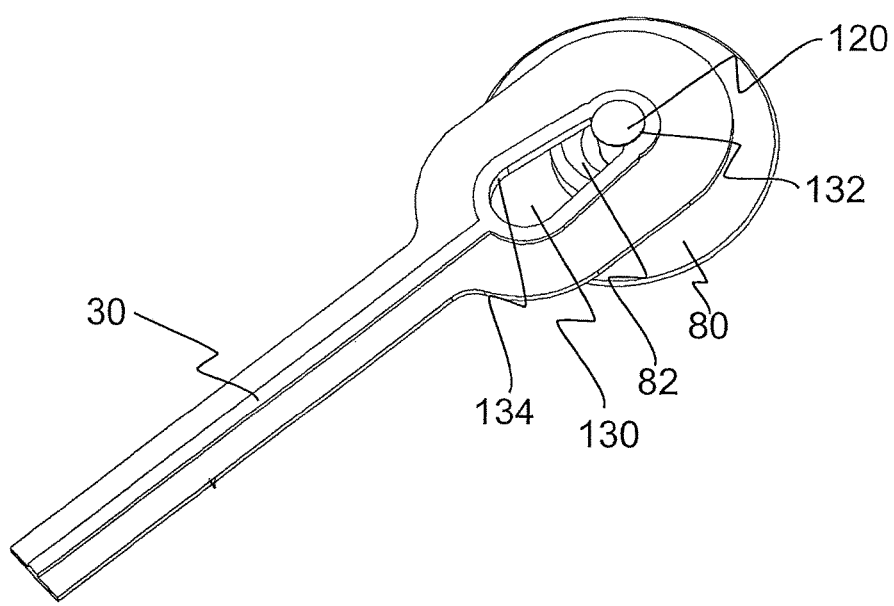
FIG. 10. Perspective view of a locking connector and electrode used in various embodiments of the present invention.

FIG. 10 shows a perspective view of a locking connector and electrode used in various embodiments of the present invention. The lockable connector 30 shown in FIG. 10 comprises a key hole 130 which allows for a stud 120 from a button connector 82 of a gel-type electrode 80 to be inserted through the connector 30, and a narrowed collar area 132 which applies pressure to the neck (not shown) of the stud 120 and effectively locks the stud 120 into the connector 30. The key hole 130 also having an electrical pathway 134 to hold the connector 30 in electrical connection with the stud 120 of the button connector 82.

Figure 11:
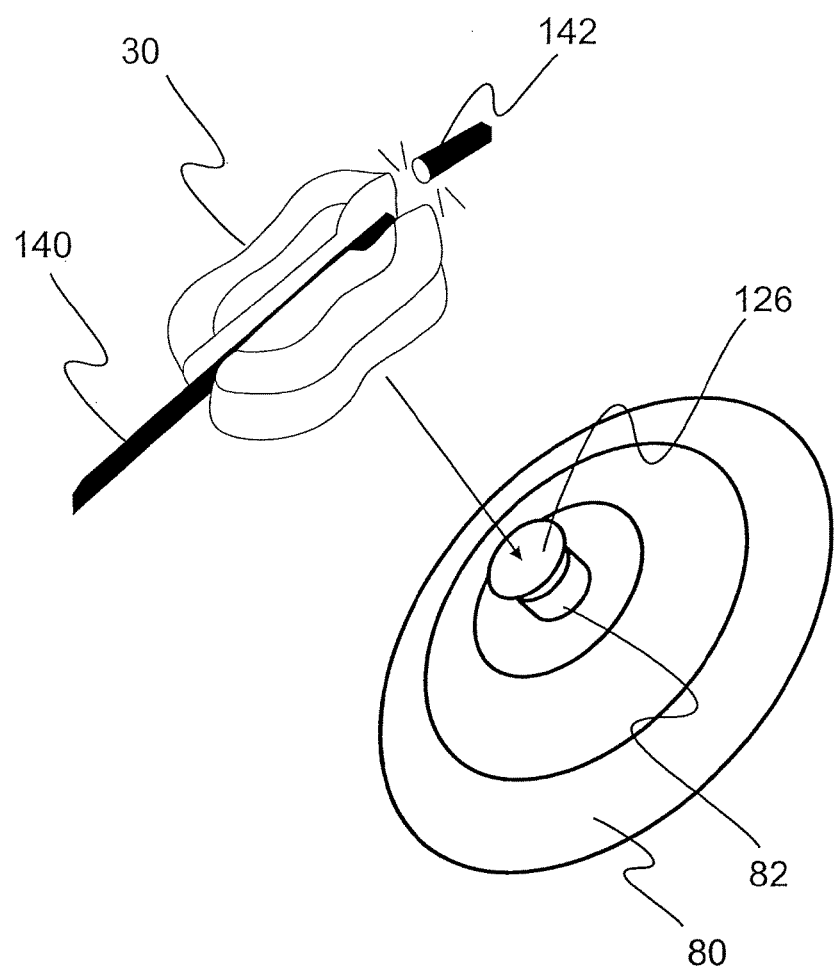
FIG. 11. Perspective view of another embodiment of a locking connector and electrode used in various embodiments of the present invention.

FIG. 11 shows a perspective view of another embodiment of a locking connector and electrode used in various embodiments of the present invention. The locking, adjustable connector 30 is used to effectively lock the stud 126 of the button connector 82 into the connector, and through the same action and time the connector makes electrical connection with the lead wire 140 to the connector and cuts off any excess wire 142.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. An electrode harness for physiological monitoring of a subject, the electrode harness comprising
   at least one dry electrode with adjustable connector;
   a material operable to mechanically and electrically interconnect at least two electrodes; and
   a track system attached or integral to the material
   wherein the at least one electrode is movable along the track system with the adjustable connector.

2. The electrode harness in claim 1, wherein the material is a multi-layer laminate.

3. The electrode harness in claim 2, wherein the material comprises at least two expandable arms, each of the at least two expandable arms corresponding to the at least two electrodes.

4. The electrode harness in claim 3, wherein the material further comprises a slit or a mechanical weak point for separating one of the electrodes.

5. The electrode harness in claim 1, wherein the material comprises at least two expandable arms, each of the at least two expandable arms corresponding to the at least two electrodes.

6. The electrode harness in claim 1, further comprising at least one additional electrode wherein the material comprises an electrical pathway from each of the at least one and at least one additional electrodes, the electrical pathway being electrically shielded from large defibrillator voltages.

7. An electrode harness for physiological monitoring of a subject, the electrode harness comprising:
   at least two dry electrodes;
   a material operable to mechanically and electrically interconnect the at least two electrodes comprising separate electrical pathways to each of the at least two dry electrodes; and
   a lead connector to mechanically connect the material and electrically connect the separate electrical pathways to each of the at least two dry electrodes of the electrode harness to a tether or a wireless transmitter,
   wherein at least one of the at least two dry electrodes are each connected to the material with an adjustable connector.

8. The electrode harness in claim 7, wherein the material is a multi-layer laminate.

9. The electrode harness in claim 8, wherein the material further comprises a slit or a mechanical weak point for separating one of the electrodes.

10. The electrode harness in claim 8, wherein the material comprises at least two expandable arms, each of the at least two expandable arms corresponding to the at least two electrodes.

11. The electrode harness in claim 7, wherein the material comprises at least two expandable arms, each of the at least two expandable arms corresponding to the at least two electrodes.

12. The electrode harness in claim 7, wherein the material comprises an electrical pathway from the at least two dry electrodes, the electrical pathway being electrically shielded from large defibrillator voltages.

13. The electrode harness in claim 7, further comprising a track system attached or integral to the material wherein at least one electrode is movable along the track system with the adjustable connector.

14. An electrode harness for physiological monitoring of a subject, the electrode harness comprising:
   at least two dry electrodes;
   a material operable to mechanically and electrically interconnect the at least two electrodes comprising separate electrical pathways to each of the at least two dry electrodes; and
   a lead connector to mechanically connect the material and electrically connect the separate electrical pathways to each of the at least two dry electrodes of the electrode harness to a tether or a wireless transmitter,
   wherein at least one of the at least two dry electrodes are each connected to the material with an adjustable connector and the material further comprises a slit or a mechanical weak point for separating one of the electrodes.

15. The electrode harness in claim 14, wherein the material comprises at least two expandable arms, each of the at least two expandable arms corresponding to the at least two electrodes.

16. The electrode harness in claim 14, wherein the material comprises an electrical pathway from the at least two dry electrodes, the electrical pathway being electrically shielded from large defibrillator voltages.

17. The electrode harness in claim 14, wherein each of the at least two dry electrodes is connected to the material with an adjustable connector.

18. The electrode harness in claim 17, further comprising a track system attached or integral to the material wherein at least one electrode is movable along the track system with the adjustable connector.

* * * * *